United States Patent [19]

Olson et al.

[11] 4,012,291
[45] Mar. 15, 1977

[54] ELECTROCHEMICAL OLEFIN DETECTOR FOR GASEOUS STREAMS

[75] Inventors: Donald C. Olson, Florissant, Mo.; Michael P. Guillory, La Place, La.

[73] Assignee: Shell Oil Company, Houston, Tex.

[22] Filed: July 25, 1975

[21] Appl. No.: 599,267

Related U.S. Application Data

[63] Continuation-in-part of Ser. No. 501,513, Aug. 29, 1974, Pat. No. 3,960,690.

[52] U.S. Cl. ............................................. 204/1 T
[51] Int. Cl.² ..................................... G01N 27/46
[58] Field of Search ............... 204/1 K, 1 T, 195 R

[56] References Cited
UNITED STATES PATENTS 2,862,859  12/1958  Grosskopf .................... 204/195 R
3,146,181  8/1964   Bell ............................... 204/195 W
3,305,457  2/1967   Hyman .......................... 204/195 R
3,432,403  3/1969   Glass et al. .................... 204/195 R
3,519,547  7/1970   Paulik et al. .................. 204/195 R
3,824,167  7/1974   Oswin et al. ..................... 204/1 K

*Primary Examiner*—T. Tung

[57] ABSTRACT

A method for measuring the quantity of olefins present in a hydrocarbon stream wherein a measured quantity of the hydrocarbon is injected into a vaporizing furnace. A carrier gas transports the vaporized hydrocarbon through the furnace to an electrochemical cell whose signal is integrated to provide a measure of the olefins present in the sample.

2 Claims, 1 Drawing Figure

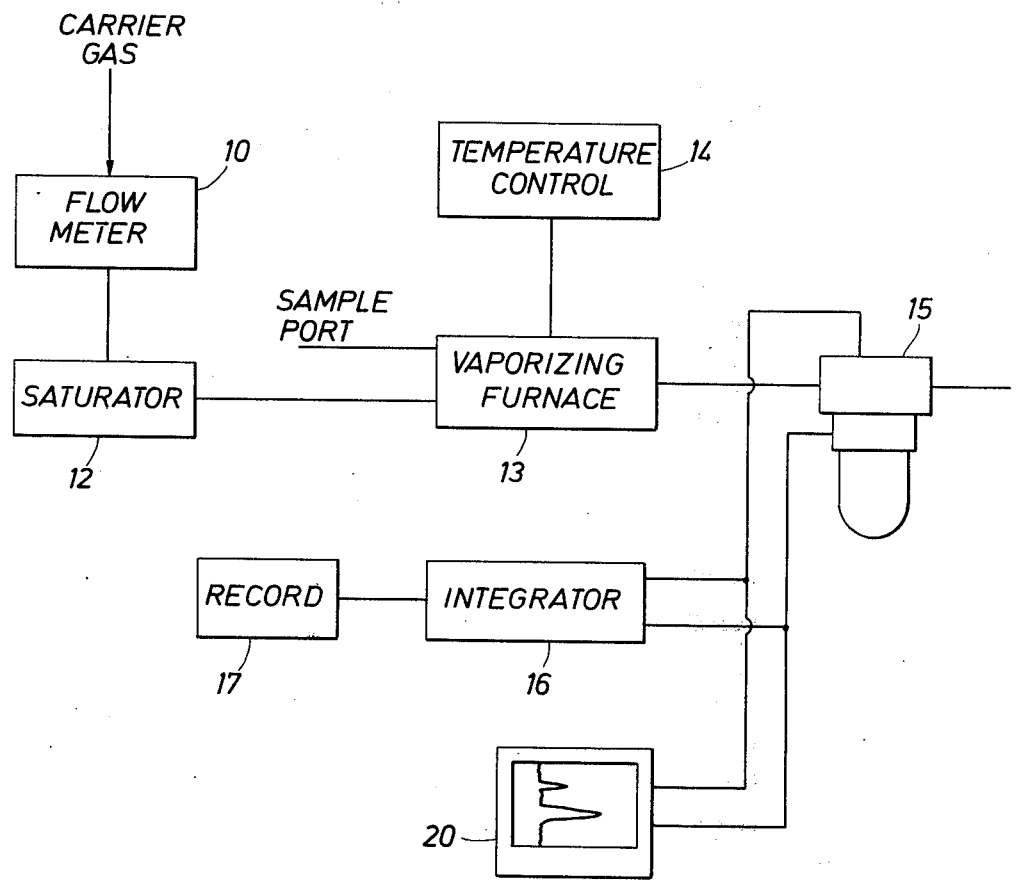

ELECTROCHEMICAL OLEFIN DETECTOR FOR GASEOUS STREAMS

RELATED PATENT APPLICATION

The present application is a continuation-in-part of an application by the same inventors titled "ELECTROCHEMICAL DETECTOR FOR LEAD ALKYLS IN GASEOUS STREAMS", Ser. No. 501,513, filed Aug. 29, 1974, now U.S. Pat. No. 3,960,690.

BACKGROUND OF THE INVENTION

The present invention relates to a method utilizing the apparatus disclosed in the above referenced patent application for measuring the olefins present in a hydrocarbon stream. Te co-pending application discloses an electrochemical cell having an electrolyte which renders the cell sensitive for measuring trace amounts of lead alkyls in gaseous streams. The apparatus includes a means for filtering out or at least delaying the arrival of olefins in the gaseous streams at the electrochemical cell.

The present invention utilizes the above apparatus for detecting olefins in hydrocarbons. The most commonly used method for analyzing hydrocarbons for the presence of olefins is a gas chromatograph unit which separates the hydrocarbon stream into its components which can then be detected to provide a record of the quantity of each type of hydrocarbon in the stream. While this is satisfactory, it has a disadvantage of requiring a relatively long time to run a sample plus an overlap of signals from some olefins and aromatic hydrocarbons which confuse the resulting data.

BRIEF SUMMARY OF THE INVENTION

The method of the present invention solves the above problems of obtaining a quick and accurate measurement of the quantity of olefins present in the hydrocarbon stream by utilizing a portion of the apparatus of the above co-pending application. More particularly, the method utilizes the furnace for vaporizing the hydrocarbon sample and an electrochemical cell for measuring the quantity of olefins present in the vaporized sample. The method does not require the use of a column or other means for separating out any of the components since the electrolyte is chosen to react primarily with olefins and only to a minor extent with other hydrocarbon components such as aromatics. The electrolyte may be of various types but an electrolyte formed of $HgSO_4$ dissolved in $H_2SO_4/H_2O$/dioxane has been found to be particularly satisfactory.

The method requires very little time to perform since the sample is injected directly into the vaporization furnace and transported by a carrier gas to the electrochemical cell with no time delay in the separation column or other apparatus. The measurement of the olefinic content of a hydrocarbon stream can be obtained in 2–3 minutes under normal conditions.

BRIEF DESCRIPTION OF THE DRAWING

The invention will be more easily understood from the following detailed description of a preferred embodiment when taken with the attached drawing showing in block diagram form one apparatus suitable for carrying out the method of this invention.

PREFERRED EMBODIMENT

Referring to the drawing, there is shown the basic instrument shown in the co-pending application except for the elimination of the aromatics and olefin filter shown in the co-pending application. The apparatus includes a flow meter for providing a constant flow of carrier gas and a saturator 12 for saturating the carrier gas with water. The use of a saturator is not absolutely necessary but is preferred since it provides more uniform results when the electrolyte and wick element of the measuring cell is changed as explained in the co-pending application. The carrier gas is supplied to a vaporizing furnace 13 whose temperature is controlled by a controller 14. Also supplied to the vaporizing furnace are measured samples of the hydrocarbon stream whose olefin content is being measured. The sample can be measured by means of a syringe and then injected into the furnace through a self-sealing port. Likewise, suitable valves may be used so that the carrier gas can be switched to transport the sample through the furnace to the measuring cell.

The vaporized sample of the furnace is passed through the measuring cell 15 which comprises a reservoir of electrolyte and a saturated disc and wick for transporting the electrolyte to the disc. An electrode is positioned on each side of the disc to measure the current produced by the electrochemical reaction of the olefins in the vaporized sample with the electrolyte. The signal from the cell can be supplied to an integrator 16 and recorded on a recorder 17 that can be a digital recorder or an analog recorder. The signal may also be supplied to a conventional chart recorder 20 which will record the amplitude of the signal with relation to time so that the area under the curve can be measured to determine the amount of olefins present in the sample.

As explained above, the electrolyte is chosen to respond primarily to olefins and only to a minor extent to aromatics and other constituents of the hydrocarbon stream. A suitable electrolyte has been found to be the following $HgSO_4$ dissolved in $H_2SO_4/H_2O$/dioxane.

In addition to the above, the following electrolytes are also useful $AgNO_3$, $AgBF_4$, or other silver salts dissolved in an alcohol/water solvent.

In operation the instrument is first calibrated by use of a known hydrocarbon sample, by injecting 10 to 15 microliters into the vaporizing furnace. The carrier gas is then used to transport the vaporized hydrocarbon sample to the electrochemical cell. The vaporized hydrocarbon flows through the cell and exits from the cell producing a current proportional to the quantity of olefins present in the sample. This current is measured by the electrodes which are positioned on opposite sides of the pad saturated in the electrolyte. This current can then be integrated to obtain a measurement of the total quantity of olefins present or recorded on a chart recorder. After the instrument is calibrated using the known sample, the unknown sample can be injected and the process repeated. Of course, it is also possible to use the current as a control signal for controlling the process that uses the quantity of olefins present in a stream as one of the constraints or measured variables in the control process.

We claim as our invention:

1. A method for measuring the quantity of olefins present in a hydrocarbon sample comprising:
    vaporizing a sample of the hydrocarbon sample;

passing the vaporized sample to an electrochemical cell, said cell being filled with an electrolyte comprising a solution of $HgSO_4$ in $H_2SO_4/H_2O$/dioxane; and measuring the current produced by the cell.

2. A method for measuring the quantity of olefins present in the hydrocarbon sample comprising:

vaporizing a sample of the hydrocarbon sample;

passing the vaporized sample to an electrochemical cell, said cell being filled with an electrolyte comprising a solution of a soluble silver salt dissolved in an alcohol water/solvent; and measuring the current produced by the cell.

* * * * *